(12) United States Patent
Steg et al.

(10) Patent No.: US 8,678,355 B2
(45) Date of Patent: Mar. 25, 2014

(54) DEVICE FOR HUMIDIFYING BREATHING AIR FOR ARTIFICIAL RESPIRATION

(75) Inventors: Helge Steg, Stockholm (SE); Leif Hall, Norsborg (SE)

(73) Assignee: Arta Plast AB, Tyreso (SE)

( * ) Notice: Subject to any disclaimer, the term of this patent is extended or adjusted under 35 U.S.C. 154(b) by 516 days.

(21) Appl. No.: 12/939,368

(22) Filed: Nov. 4, 2010

(65) Prior Publication Data

US 2011/0156289 A1    Jun. 30, 2011

(30) Foreign Application Priority Data

Nov. 6, 2009   (EP) .................................... 09013976
Sep. 24, 2010  (EP) .................................... 10010536

(51) Int. Cl.
*B01F 3/04*      (2006.01)
(52) U.S. Cl.
USPC ........ 261/57; 261/64.3; 261/66; 261/DIG. 65
(58) Field of Classification Search
USPC .............. 261/54, 55, 56, 57, 63, 64.5, 66, 70, 261/119.1, DIG. 65
See application file for complete search history.

(56) References Cited

U.S. PATENT DOCUMENTS

| 1,227,539 | A | * | 5/1917 | Illsley ........................... 137/432 |
|---|---|---|---|---|
| 2,561,580 | A | * | 7/1951 | Lepicard ...................... 137/425 |
| 3,806,102 | A | * | 4/1974 | Valenta et al. ................. 261/142 |
| 4,192,836 | A |   | 3/1980 | Bartscher et al. |
| 4,225,542 | A | * | 9/1980 | Wall et al. ...................... 261/142 |
| 4,366,105 | A |   | 12/1982 | Nowacki |
| 5,195,515 | A |   | 3/1993 | Levine |
| 5,943,473 | A | * | 8/1999 | Levine .......................... 392/401 |
| 6,988,497 | B2 | * | 1/2006 | Levine ..................... 128/203.27 |
| 7,722,016 | B2 | * | 5/2010 | Bradley et al. .................. 261/70 |
| 8,181,938 | B2 | * | 5/2012 | Payne et al. ....................... 261/5 |
| 8,210,177 | B2 | * | 7/2012 | Payne et al. .............. 128/205.24 |
| 2004/0050386 | A1 |   | 3/2004 | Levine |
| 2008/0054500 | A1 |   | 3/2008 | Bradley et al. |

OTHER PUBLICATIONS

International Search Report in PCT/EP2010/006773, Jul. 6, 2012.
European Search Report in EP 10 01 0536, Nov. 16, 2011.

* cited by examiner

*Primary Examiner* — Charles Bushey
(74) *Attorney, Agent, or Firm* — Bacon & Thomas, PLLC (57) ABSTRACT

A device for humidifying breathing air for artificial respiration of mammals, in particular human beings, includes at least one essentially closed container for receiving water, a first opening for letting in the non-humidified air and a second opening for letting out humidified air, and an inlet for supplying the water to the container. The inlet is located in the upper part of the container, which is adjoined by a tube essentially crossing through the container interior, and on the free end of the tube, a valve is disposed, which limits the level of the water supplied via the tube in such a way that the container bottom in the container interior is essentially covered with water.

23 Claims, 6 Drawing Sheets

Fig. 6

DEVICE FOR HUMIDIFYING BREATHING AIR FOR ARTIFICIAL RESPIRATION

BACKGROUND OF THE INVENTION

1. Field of the Invention

The invention relates to a device for humidifying breathing air for artificial respiration of mammals, in particular of humans, that includes at least one essentially closed container for receiving water, a first opening in the container for letting non-humidified air in, a second opening for letting the humidified air out, and an inlet for supplying water to the container.

2. Related Art

Devices of this type which in medical terminology are simply called air humidifiers, and in the English-speaking world "humidifiers", are employed both in outpatient care and in the hospital. As the term used for the device implies, humidifiers are employed for humidifying breathing air in case humans, but also animals, must be artificially provided with air for the most diverse reasons or purposes, or air that must be supplied in addition to normal breathing air. It is known that air for artificial respiration, made available either from air bottles which are under pressure, or directly by means of pumping devices, as a rule do not have the degree of moisture required for the gentle application of artificial respiration to a human or to an animal. A multitude of devices (humidifiers) of the type mentioned at the outset are known in the prior art, all of which have the above mentioned basic typical construction to a greater or lesser extent. Since in the prior art the basic construction of these devices, the areas of their application, and the specific applications of humidified breathing air for humans and for animals are well known, further discussion thereof is not required.

But to the extent that can be observed, the known devices all have one and/or the other disadvantage, which will be separately addressed below. It is obvious that in their operation, that is, in the course of their application for the humidifying of breathing air, these devices are not permitted to exhibit any shortcomings or interferences regarding their functioning. A major problem, which was intended to be overcome in many different constructions, is that in all cases the humidified breathing air leaving the device must not contain water being used in the device for humidifying the air, which could get into the lungs of the human or animal via the breathing air connection between the device and the human or animal. Without addressing this in greater detail, this could have severe consequences, even death, for the human or animal to be supplied with air.

To prevent this, valve structures of various different types have been proposed in the humidifier container which are intended to prevent water, which is picked up for humidifying, to escape from the container together with the humidified breathing air through the outlet and to reach the human or animal to be supplied with air. The solutions proposed up to now that are intended to solve or overcome this problem have the disadvantage, which is unacceptable under any circumstances because of the damage to health connected therewith, that they are all essentially based on the principle that, although a predefined amount of water is always being received in the container and replenished (since the water in the container is used up by becoming absorbed in the air passed through the container) nevertheless, in case of malfunction of the device that controls the replenishment of the water in the container, the device may fail to prevent water from reaching the human or animal whose breathing is to be aided via the outlet for the humidified air, with the disadvantageous results mentioned above, which are often fatal.

SUMMARY OF THE INVENTION

It is therefore an object of the invention to provide a device of the type mentioned at the outset, by means of which it is possible by simple means and a simple construction to provide the continuously reliable functioning of the device, so that the uncontrolled supply of water to the container is prevented, even in the event of a malfunction, so that in any case, water cannot reach the outside via the outlet to the exterior for the humidified air, or reach the human or animal to be given artificial respiration.

This object is attained in accordance with the invention in that the water inlet is formed in the upper part of the container, to which is connected a tube, which essentially crosses through the interior of the container, and a valve is arranged on the free end of the tube, which limits the level of the water supplied via the tube in such a way that the interior container bottom is essentially covered with water.

This extremely advantageous principle permits a construction of the device in the interior of the container in such a way that, in case of a malfunction, when water has reached the said predetermined level in the interior of the container, the water does not have any access to the part of the container between the inlet for non-humidified air and the outlet for humidified air. By means of this proposed step the level of the water supplied via the tube can be limited in such a way that only the container bottom in the interior of the container is covered with water, or in other words covered up to a few millimeters high in relation to the container bottom.

The way the invention attains this object has proved to be extremely safe and also meets the legal requirements and parameters for such devices.

In accordance with an advantageous embodiment of the humidifying device, the valve has an essentially cylindrical portion, by means of which it is received in the free end of the tube, and an essentially platelike portion with which, in a base position, closes off the opening in the free end of the tube. For supplying water to the container interior, the platelike portion of the valve is slightly deformed by the flow of water through the tube in the course of the filling process because of the pressure of the water being slightly higher than that prevailing in the container interior, so that as much water can enter as the interior pressure in the container interior normally permits.

Preferably, the cylindrical portion of the valve has a plurality of axially extending grooves, through which the water supplied via the tube can flow over the platelike portion, as described above, and flow into the container interior up to the desired height.

Finally, the valve is preferably made of an elastomer material, for example silicone rubber, which is employed without problems in medicine, and which has the advantage that it can be made highly resilient, so that the platelike portion in particular can perform its intended opening and closing functions free of malfunctions over long periods of time, but still can assure secure seating in the tube by means of its cylindrical portion.

In a further, different advantageous embodiment of the humidifying device, a means is provided which, as a function of the level of the water in the partial interior space, provides a short circuit, in the manner of a bypass between the inlet for the non-humidified air and the outlet for the humidified air, that puts the partial interior space out of contact with the water vapor above the surface of the water and, when the level drops, again brings the partial interior space into communication with the water. The dropped level mentioned in this connection need not be absolutely the equal of the level which, in connection with the attainment in accordance with the invention, limits the water in the container interior supplied via the tube. However, in a certain still more different embodiment of the invention, it could easily be possible for these two water levels to be of equal height. In this advantageous embodiment of the humidifying device, a short circuit is virtually provided in this case between the inlet for the air admitted into the container and the outlet of the air out of the container, in which case only the remaining moisture in this short-circuited area is then used as the humidifying means, while, in accordance with the invention, escape of water from the device from the outlet for the humidified air is prevented. In this case, the brief application of non-humidified breathing air, or of such air only containing residual moisture, is as a rule harmless, and furthermore takes place only long enough for the level of the water to fall below said predetermined level, or to be lowered because of outside influences.

In accordance with an advantageous embodiment of the humidifying device, the means includes a float device which floats in the container interior on the water therein and, upon reaching a predetermined level, bumps against a first sealing element connected with the container, and because of this interrupts the supply of water to the container. The advantage of this embodiment of the means is that no lever elements and hinges are present, which tend to exhibit malfunctions in a watery environment, so that by this step too, as required at the outset, besides the satisfactory and assured functionality, a simple and therefore also cost-effective embodiment of the humidifying device is possible, because in many cases it is only required once, and must then be disposed of in order to prevent the transfer of germs.

In this connection it is advantageous that the float arrangement of the humidifying device has a collarlike element, which bumps against the first sealing element connected with the container once the predetermined maximum level of the water in the container has been reached. Because of this, that is, in the state in which the collarlike element has bumped against the first sealing element, the inlet for the air into the container and the outlet for the air from the container are advantageously essentially enclosed via a remaining partial interior space; that is, a bypass, is formed, so to speak, for the air from the inlet for the air into the container and the outlet for the air from the container, so no water can enter into this bypass space, that is, the remaining partial interior space and, as already mentioned generally above, although the humidified air to be applied can only stem from the remaining moisture in the partial interior space, no water can enter the outlet for the air out of the container for supplying air for breathing to a human or an animal. This structure, too, is free of movable parts and can therefore be made available in a functionally safe and also cost-effective manner.

In accordance with a further, different advantageous embodiment of the humidifying device, the tube, which is essentially centrally located for the supply of water to the container, essentially extends into the bottom area of the container, and in this embodiment the float device preferably has an essentially central passage, which can be embodied in the form of a central interior tube, in which the central tube extends. Here, the central tube also has a guide function, so to speak, for the float device and a guidance function for the water to be introduced from the outside into the container interior, and here, too, there is again the advantage that no links, hinges or lever elements or the like are present for blocking the water, such as those used with devices known in the prior art. Accordingly, on the one hand a high degree of functionality is achieved, and on the other a cost-effective availability is assured.

The float device is preferably embodied as an essentially closed, floatable body, which therefore advantageously has no attachment points for being caught in the interior container chamber because of its rising and sinking movements as a function of the force of the water in the interior container chamber in relation to an essentially horizontal alignment of the container bottom as the plane of reference. In principle, this float body can also be embodied as a hollow element, and, it is also possible to use materials for its construction (see below) which have a specific gravity of <1, so that it is lighter than water and therefore will float in the water.

The above mentioned collarlike element is advantageously embodied as a part separate from the float device and is fastened on the float device, in which case this embodiment makes possible the construction of the float device, on the one hand, and of the collarlike element on the other, from different materials where, for example, the actual float body need not have any elastomeric properties, but where the collarlike element may need to be made of an elastomer material, since it has a sealing function or objective. However, it should be made clear that it is of course possible to form the collarlike element, as well as the float device, from the same material, and/or in one piece.

The second sealing element provided in still another advantageous embodiment of the humidifying device, is essentially arranged centrally in the upper container part, and is essentially formed circular in cross section and, in addition, advantageously has an essentially encircling sealing lip. In this case the sealing element is in fact embodied in one piece with the upper container part and can be formed in the course of the forming (molding) process of the upper container part. However, it can also be produced as a separate part and can be fastened in the upper container part in the course of producing the entire device, for example by means of gluing, welding, or by a molding process.

A circumferential sealing lip on the sealing element itself preferably is embodied in one piece with the sealing element and therefore can also be matched in regard to its elasticity to the individual required mechanical requirements; that is, the degree of elasticity of the sealing lip can be different from the degree of elasticity of the remainder of the sealing element.

In connection with still another very advantageous embodiment of the humidifier device in the condition where the supply of water to the container interior is interrupted, the sealing lip rests sealingly on the float device, in particular free of any additional further sealing means. That is, the float device forms one part of the seal by means of its side facing the sealing lip of the second sealing element, and the sealing lip itself forms the other part of the second seal, so that in this way the sealing means without further movable parts can be simply produced which, avoids malfunction.

In the case where the partial interior space is formed in the manner of a bypass, the second sealing lip rests sealingly on the float device, in which case, as explained above, the float device itself forms the required sealing counterpart to the sealing lip. That is, the sealing lip and the float device itself constitute the seal, so that it is possible dispense entirely with other movable or sealing parts of humidifying device structures that are prone to malfunction that have been used up to now, so that even impacts from the exterior on the humidifying device largely have no effect, because the float body is embodied in the area of the sealing lip adjoining it in such a way that even shock effects laterally acting from the outside on the device have practically no effect, or in other words do not adversely affect the sealing effect.

Advantageously, at least the sealing lip is made of an elastomer material, and the collarlike element of the float device also is advantageously made of an elastomer material. The elasticity of the sealing lip as well as of the collarlike element can be embodied in different forms, depending on the construction and use of the humidifying device, and can be matched to the structural and operational requirements of the humidifying device.

As mentioned above, the float device can be made of a metallic or also a non-metallic material however, it is advantageous to make it from a plastic material in order to produce the float device as a uniform injection-molded element made of a plastic material which, besides the low weight, the low production costs and the operational dependability to be expected, also has the advantage that it is possible to assure freedom from germs associated with the production process for the float device.

The container housing itself can also preferably be made of a plastic material, preferably from an injection-moldable plastic material, in which case preferably the inlet for the supply of water to the container and the upper container part are made in one piece; that is, the container or the container housing can in fact be produced from plastic in a single work step, in particular an injection-moldable plastic material, because of which it is already possible to assure freedom from germs by means of a production process selected in this way, and expensive procedures for making the humidifying device germ-free can be omitted to a large extent.

Not only can at least the upper container part, and/or at least the inlet for the supply of water, preferably be made of a plastic material, in particular injection-moldable plastic material, but the bottom of the container (which must be combined with the container housing after the humidifying device has been equipped with the valves and the float element before it is closed off in a watertight manner later by a metal container bottom) can advantageously also be made of a plastic material, in particular an injection-moldable plastic material, in order to assure freedom from germs in the course of producing the container, as can its individual parts to also make the humidifying device lighter and able to be disposed of more easily and therefore more cost-effectively after a one-time use as a rule, since no metallic parts are contained in the humidifying device in accordance with the invention, making and it possible to recycle the individual components of the humidifying device in the simplest way.

The container bottoms known in the prior art used in connection with humidifying devices are as a rule made of metal, or metal alloys, and these metallic container bottoms are connected as a rule by means of a comparatively elaborate connection process with the container, or the upper container part, which as a rule is made of a plastic material.

Therefore, in accordance with the invention, the container bottom is preferably made of a plastic material, which permits a very simple connection with the upper container part when the upper container part and the lower container part are made of the same plastic material.

As a rule, the water contained in the upper container part must be heated for the intended formation of steam for achieving the intended humidifying of the air; that is, it must be brought up to and maintained at the temperature which represents a temperature, or a temperature range, physiologically suitable for the intended purpose. For this purpose, the bottom areas of the heating devices are set, or pushed, onto a heating device, which enables a good heat transfer between the heating device and the container bottom.

It has been found that for this purpose a container bottom is best suited for rapid heating and the avoidance of heat losses in the course of the heating process, if it is made of a foil consisting of a plastic material. The plastic material of the container bottom is preferably polyester, in which the thickness of the container bottom preferably lies in the range between 0.05 to 0.5 mm.

DESCRIPTION OF THE DRAWINGS

The invention will now be described by means of an exemplary embodiment, with reference to the attached schematic drawings, where.

DETAILED DESCRIPTION OF PREFERRED EMBODIMENTS OF THE INVENTION

Figure 1:
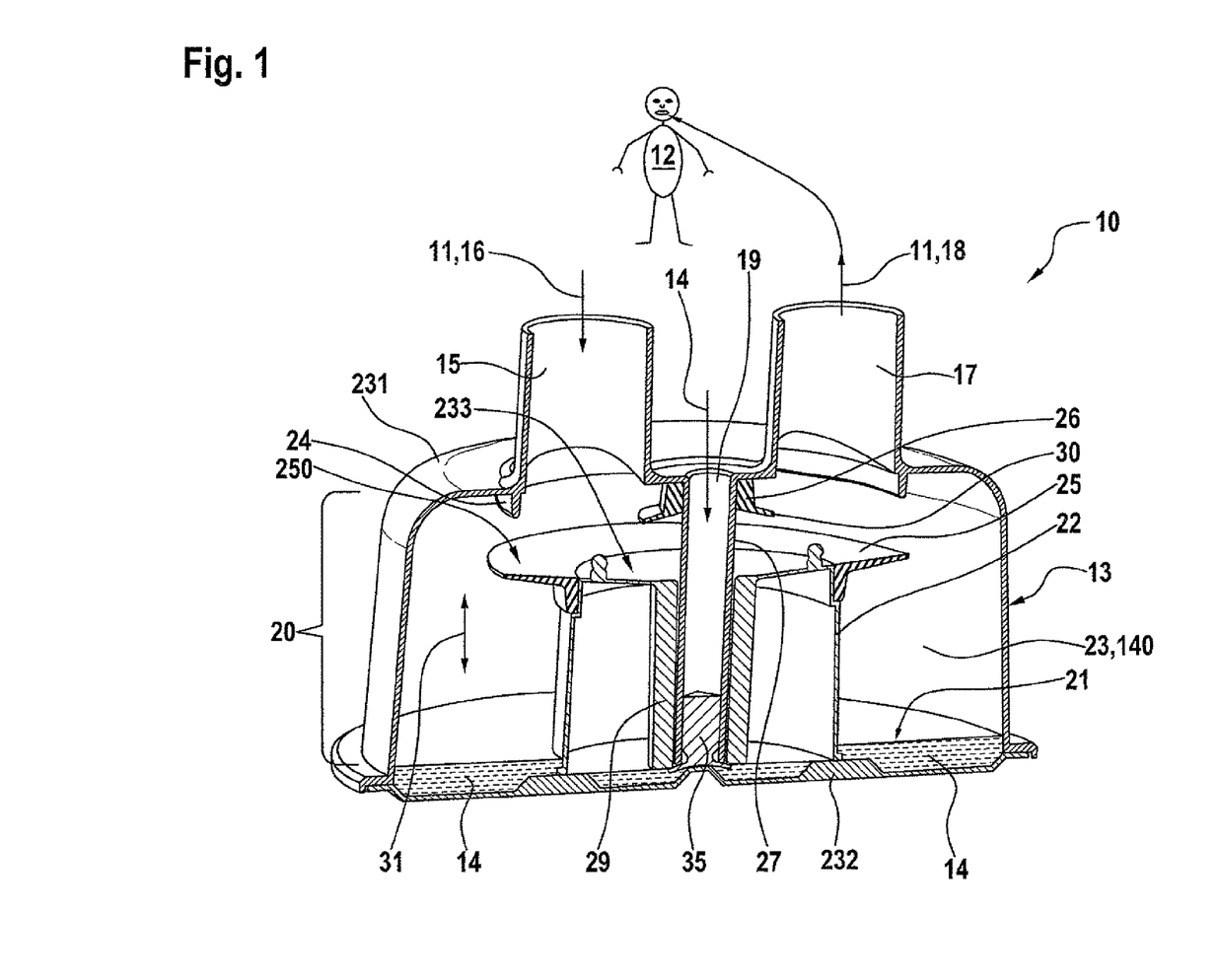
FIG. 1 shows the humidifying device in accordance with the invention in a schematic semi-sectional view, in which the essential elements of the device are visible, in a view which is slightly reduced in comparison with an actual normal size.

With reference to FIG. 1, the basic structure of the humidifying device 10 will be described.

The humidifying device 10 includes an essentially closed container 13, in which the water, which is used to humidify the breathing air, is received. The container 13 has a first opening 15, through which air 16, which is not humidified, is supplied from a separately arranged air source through a hose or the like. The humidifying device 10, moreover, has a second opening 17, through which air 18, which was humidified in the interior container chamber 23, is supplied to the human 12 or to an animal, which is to be supplied with breathing air. Finally, the humidifying device has an inlet 19 for supplying water 14 to the interior container chamber 23.

The first opening 15 for the supply of non-humidified air 16, the second opening 17 for the outlet of the humidified air 18 and the inlet 19 for the supply of water are arranged in the upper part of the container 13, called the upper container part 231. The inlet and the outlet 16, 18 for the air are here embodied in the form of connecting elements which, referring to FIG. 1, extend upwardly from the upper container part 231 in the form of small tube connectors, so that air hoses can easily be connected leading to the humidifying device 10 and air hoses leading away from the humidifying device 10 to a human 12 or an animal can easily be connected with the humidifying device 10.

The container 13 also has a container bottom 232, and the upper container part 231 and the container bottom 232 essentially constitute the container 13. In the embodiments shown in the drawings, the container 13 has only three openings, namely the first opening 15, the second opening 17, and an opening constituting the inlet 19 for the supply of water 14. However, it is also possible, not shown here, to provide further openings in the upper area of the interior container chamber 23, from which it is possible, for example, to take water samples, or to attach or insert temperature sensors for the water 14 and the humidified air 18. In cross section, the container 13, or the upper container part 231, has the shape of an inverted shallow cup. However, it should be pointed out that the shape of the container 13, or of the upper container part 231 per se, can be embodied as desired as a function of the intended useful embodiment of the humidifying device 10, for example having a rectangular cross section, or the like.

Figure 4:
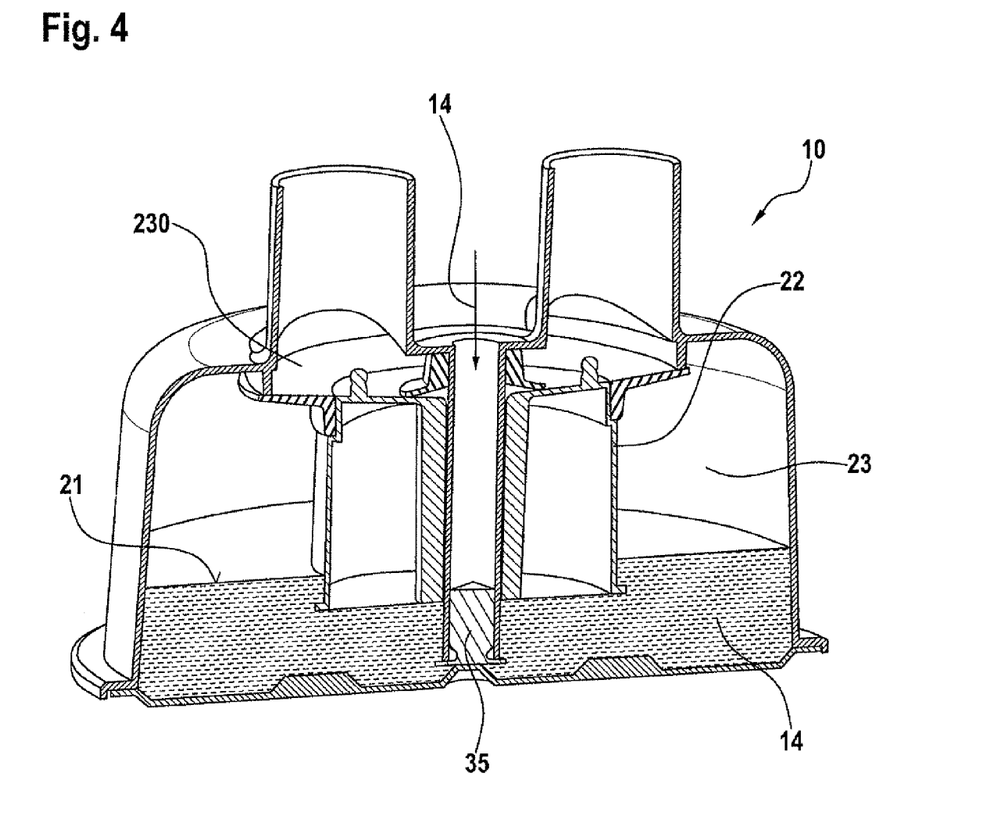

In the upper container part 231, and annularly enclosing the inlet 19 for the water 14, the first opening 15 for the non-humidified air 16, and the second opening for the outlet of the humidified air 18, there is provided a first sealing element 24, protruding in cross section from the upper container part 231 into the interior container chamber 23 and formed in the shape of a ridge, which, as shown in FIG. 4, abuts against a collar-like element 25, and is arranged at the upper end of the float device 22, as shown. This will be described in more detail further below.

In connection with the embodiment of the humidifying device shown in the drawings, the float device 22, which here is essentially embodied so as to be rotationally symmetrical in longitudinal section, is arranged in the interior chamber 23 of the container, and is intended to be a part of a means 20 which, as a function of the level 21 of the water in the interior chamber 23 of the container, can be moved back and forth vertically in the direction of the arrow 31. The first sealing element 24 also works together with the means 20, or more exactly with the float device 22. The float device 22 is made in such a way that it floats in the water 14, which water exits via the inlet 19 through a vertically extending tube 27, which is essentially centrally formed in the upper container part 231, and is located in the interior chamber 23 above the container bottom 232. The tube 27 extends in an essentially central passage 29 of the float device 22 and is guided there essentially centered by the tube 27. The guidance is such that the frictional resistance in respect to the tube 27 is very low. Therefore along the tube 27, as a function of the level 21 of the water 14, the float device 22 can move in the container interior 23 in the direction of the aforementioned arrow 31, depending on the level of water 14 in the container interior 23. The float device 22 can be made as an essentially closed, floatable body.

The means 20 or float device 22 has an encircling collarlike element 25. It is secured to the float device 22 relative to the upper regions as shown in the drawings, and essentially, with its radially oriented sealing face 250, it protrudes outward, from an imaginary central axis that passes through the tube 27, in such a way that it is below the first sealing element 24.

The means 20 furthermore includes a second sealing element 26 of elastic polymer material, which is located in the container interior in the upper container part 231, around the inlet 19 for water 14, and which in this case is essentially a rotationally symmetrical part. The collarlike element 25, too, comprises elastic polymer material. The second sealing element 26 can be made in one piece with the upper container part 231, or it can be made as a separate part and joined, in the course of assembly of the humidifying device 10, firmly and in sealing fashion to the upper container part 231. The second sealing element 26 is opposite an upper contact plane 233, in depicted in the drawings, which is radial relative to the tube 27 and protrudes away from it; this contact plane cooperates with an encircling sealing lip 30 of the second sealing element 26 and interrupts the supply of water 20 to the partial interior space 230 of the container 13 indirectly, when the first sealing element 24 rests on the radial sealing face 250 and the second sealing element 26 likewise rests on the radial sealing face 250.

Figure 2:
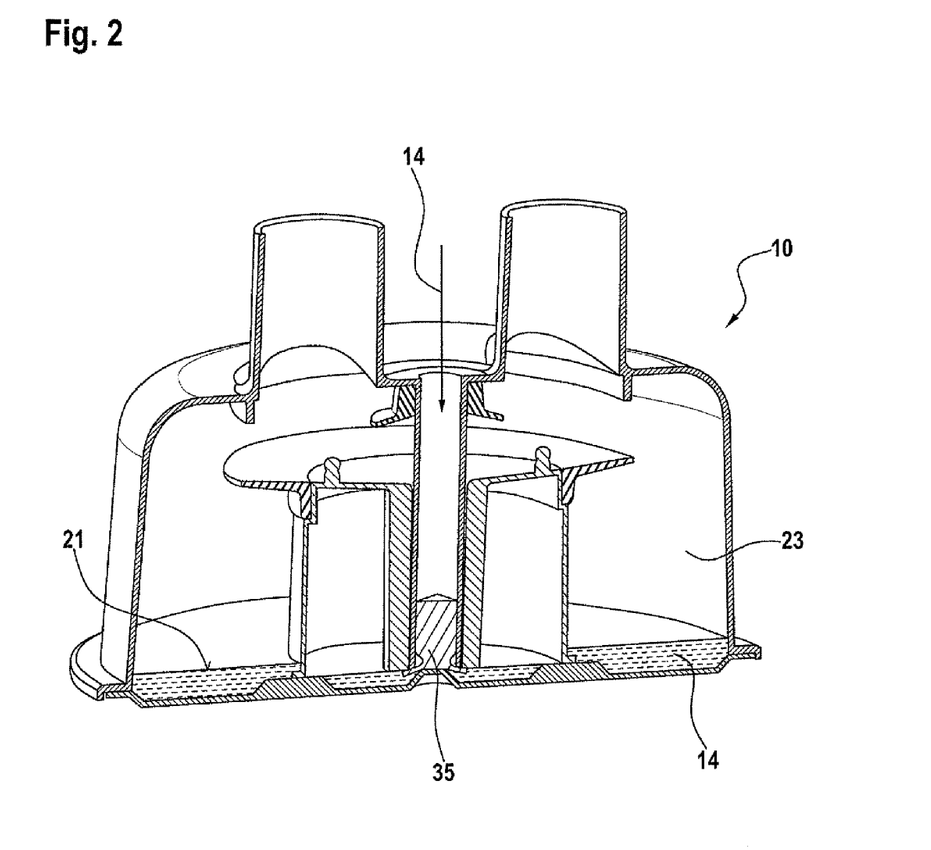
FIGS. 2 to 4 show a view in accordance with FIG. 1, in which the respective interior container chambers are filled with different amounts of water, starting in FIG. 2 with a low water content, then in FIG. 3 with an increased water content, and in FIG. 4 with the maximally possible water content, in which the flow of water into the partial interior space of the interior container chamber is interrupted.
Figure 3:
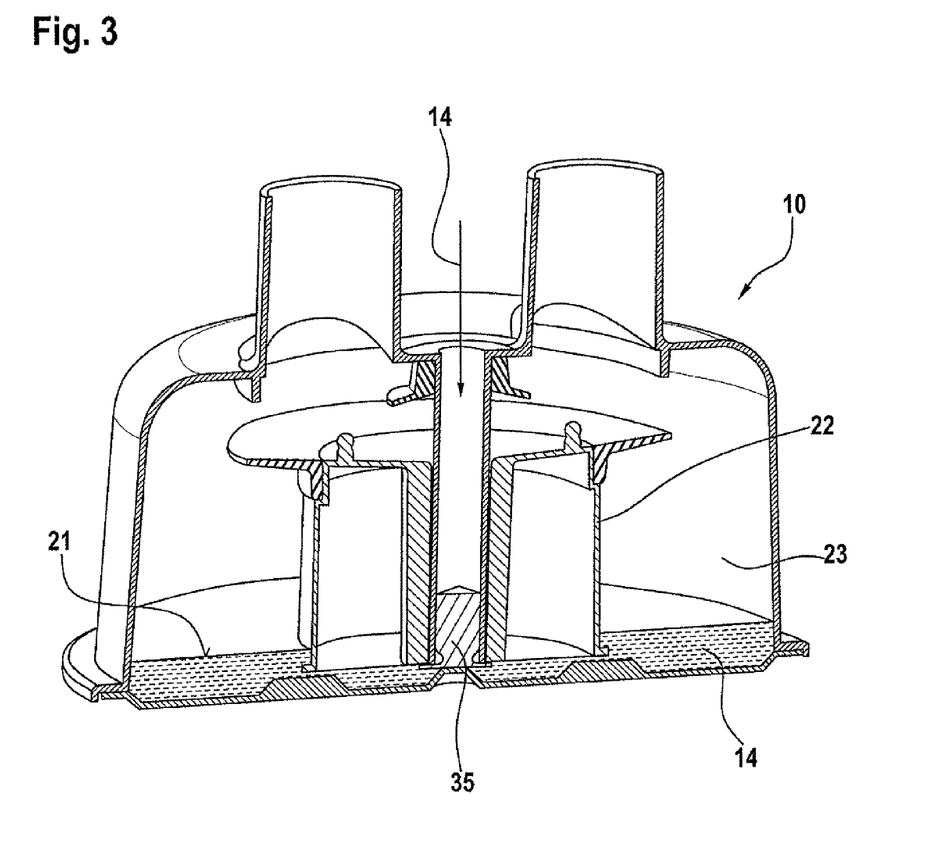

The reference numerals used in the drawings apply equally to FIGS. 2, 3, 4, 5 and 6, although some of the reference numerals have been left out for the sake of clarity, especially in FIGS. 2, 3 and 4.

FIGS. 2-4 will now be described, which show a basic or open mode for water 14, a medium water filling mode in FIG. 3, and a filled level for water in FIG. 4, in which the partial interior space 230 is closed off from the remainder of the container interior 23. FIG. 4 shows what is virtually a safety state of the device 10 for a human being or an animal, as will be discussed in detail hereinafter. The first opening 15 for letting in air and the second opening 17 for letting out the humidified air 19 each communicate with an air source 11, not shown, or with the human being 12 to be respirated, and the inlet 19 communicates with a source of water 14 for humidifying the air 11, 16, 18 in the container interior 230.

When the device 10 is started up, first water 14 is supplied, so that a certain level 21 of the water 14 is established in the container interior 23.

Figure 5:
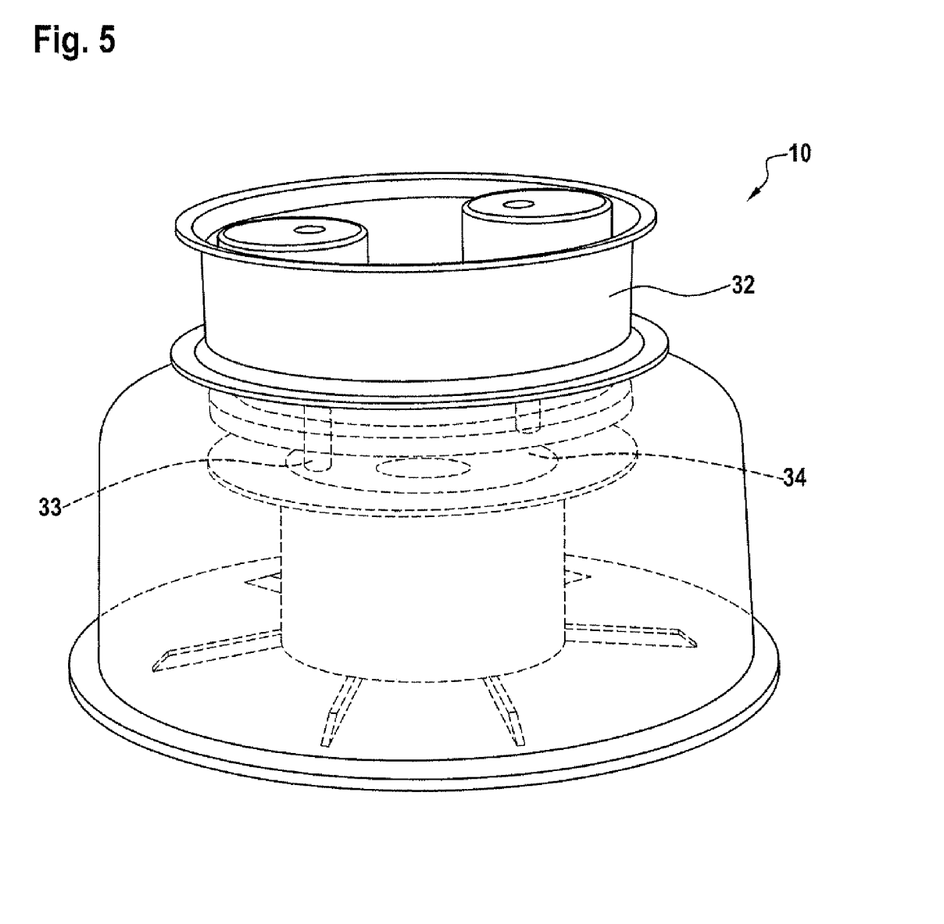
FIG. 5 shows a perspective view of the humidifying device with a removable protective ring, by means of which the air inlet and the air outlet are closed off in the storage state of the humidifying device.
Figure 6:
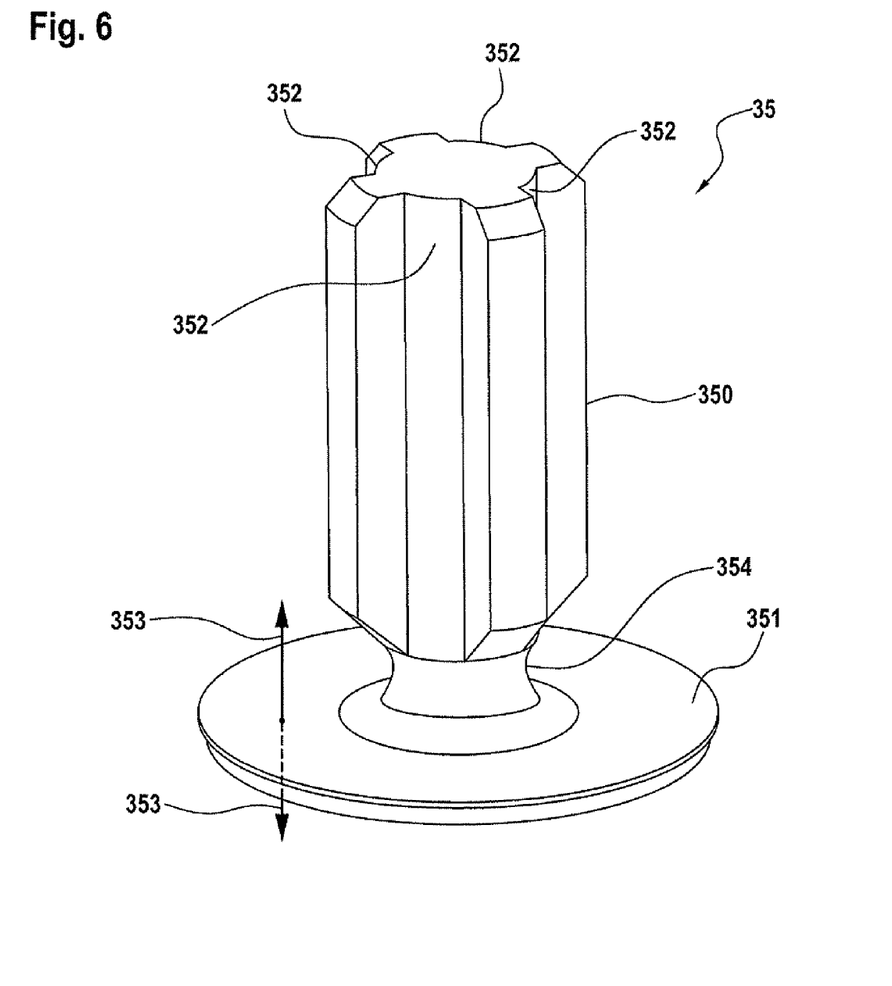
FIG. 6 shows a perspective view of the valve received in the free opening of the tube in a greatly enlarged form with the platelike portion of the valve in a relaxed state.

From a water source, not shown here, water 14 is fed into the inlet 19 of the device 10. The water source is at a pressure that is slightly higher than the pressure in the container interior 23. The water 14 strikes a valve 35 disposed on the free end 270 of the tube 27. The valve 35 is shown in FIG. 5 in terms of its basic construction. The valve 35 has an essentially cylindrical portion 350 and an essentially platelike portion 351. With its cylindrical portion 350, the valve 35 is seated in the free end 270 of the tube. With the platelike portion 351, the opening 271 of the free end 270 of the tube 27 is closed. At least the platelike portion 351 of the valve 35 comprises a highly elastic elastomer material, such as silicone rubber.

The cylindrical portion 350 of the valve 35 has a plurality of axially extending grooves 352, through which water can flow in the direction of the opening 271 of the free end 270 of the tube 27.

Since the pressure in the container interior 24, that is, in an initially water-free state, is initially set such that the external pressure, with which the water, by way of the valve 35 and with the attendant slight pivoting of the platelike portion downward, in terms of FIG. 5, flows in the direction of the arrow 353, is greater, water 14 is guided via the valve 35 into the container interior 23 until such time as the level 21 of the water supplied via the tube 27 at which the container bottom 232 in the container interior 23 is essentially covered with water is reached. The level 21 is determined by the mechanical construction of the device 10 and by the prevailing or desired pressure conditions of not only the water 14 supplied but also of the breathing air 11 supplied, or of the humidified air 18 that is carried away.

If the container bottom 232 is covered with water 14, once a certain level 21 is reached, the pressure in the container interior 23 will have increased as a consequence, so that the platelike portion 351 moves upward, in terms of FIG. 5, in the direction of the arrow 353, so that the platelike portion 351 closes the opening 271 of the free end 270 of the tube 27, and no further water can enter the container interior 23. This is the normal operating state of the device 10, as shown in FIG. 2. For the process of humidifying the breathing air 11 as it passes through the device 10, it suffices if only the container bottom 323 be covered with water 14, to at most a few millimeters deep. This also limits the energy required for heating the water 14, to generate the water vapor 140 in the container interior.

If water is improperly supplied to the device 10, for instance due to the device 10 being operated incorrectly or because the valve 35 (that is an important function element of the device) 10 is defective, the situation can arise in which water 14 undesirably enters the container interior 23 by the way described above.

With water 14 flowing in, the level 21 of the water 14 in the container interior 23 will rise, so that the float device 22, as part of the means 20, moves upward in the direction of the arrow 31 in FIG. 3. If water 14 continues to be supplied, the level 21 of the water 14 in the container interior 23 rises, and the float device 22, with its collarlike element 25 or in other words the sealing face 250 of the collarlike element 25, bumps against the first sealing element 24. Even if water continues to be supplied, the float device 22 cannot rise farther upward in the direction of the arrow 31, because the motion is limited in the vertical direction, in terms of the drawings, by the contact of the first sealing element 24 with the collarlike element 25 of the float device 22. When the collarlike element 25 has bumped against the first sealing element 24, the inlet of the air 16 into the container 13 and the outlet of the air 18 from the container 13 are short-circuited, essentially in the manner of a bypass, via a remaining partial interior space 230, so that the air 18 necessary for the artificial respiration can be carried from the second opening 17 and supplied to the person 12 or animal. In this case, the breathing air 11 is not humidified, since the course via the bypass does not permit any contact with the water vapor 140 in the container interior 23. Because of the essentially simultaneous contact of the second sealing element with the collarlike element 25, no water 14 can get into this remaining partial interior space 230, since the second sealing element 26 also enters into sealing engagement with a correspondingly embodied surface—see above—of the float device 22 and thus preventing the water 14 from entering the partial interior space, as shown in FIG. 4, via the passage 29 between the tube 27 and the float device 22.

Thus in accordance with the invention, during continuous operation, and depending on the level 21 of the water 14 in the container 13, the flow of water 14 into the container 13 is interrupted on reaching a predetermined level 21, and the flow of water 14 into the container 13 is permitted if the level 21 is not reached. If problems arise in the course of operation of the device 10, in which water 14 is introduced into the container interior 23 beyond the desired level 21, the access of the water 14 to the partial interior space 230 is prevented so that the breathing air 11 for a person 12 of an animal does not contain water 14. Thus according to the invention, no complicated valve parts, which are vulnerable to malfunction, are needed in order to ensure that water never reaches the vicinity of the outlet for the humidified air 18, and thus one can speak of a quasi-self-regulating system.

In the embodiment of FIG. 5, the humidifying device 10 of the invention is provided with a removable shipping securing means or shipping cap 32, which during storage and shipment, and also when the device happens not to be in use, covers the vicinity of the tube neck of the first opening 15 or air inlet, the vicinity of the second opening 17 or air outlet, and the vicinity of the inlet 19 for the water 14, this last not being directly visible in FIG. 5. Together with the shipping cap 32, rodlike projections that protrude through the first opening 15 and the second opening 17 can be provided, which in this state, as a virtual shipping holder 33, 34, keep the float device 22 pressed against the container bottom 232. If the shipping cap 32 is pulled off upward, by a slight pull in the direction of the arrow 31, the first opening 15 and the second opening 17 as well as the air inlet 19 for water 14 are uncovered, and simultaneously, the two rodlike shipping holders 33, 34 joined to the shipping cap 32 are removed, and the humidifying device 10 is then available for its intended use.

The invention claimed is:

1. A device for humidifying breathing air for artificial respiration of mammals, comprising:
   at least one essentially closed container for receiving water, the container having an interior;
   a first opening for letting non-humidified air into the interior and a second opening for letting out humidified air from the interior, and a water inlet for supplying the water to the container,
   wherein the water inlet is provided in an upper part of the container, which is adjoined by a tube essentially crossing through the container interior, and
   a valve disposed on a free end of the tube, said valve being configured to limit the level of the water supplied via the tube in such a way that the container bottom in the container interior is maintained essentially covered with water,
   wherein the valve has an essentially cylindrical portion that is received in the free end of the tube, and a sealing face on a bottom portion of the cylindrical portion forming a platelike portion, wherein said platelike portion is configured to close the opening of the free end of the tube, and
   wherein the cylindrical portion has a plurality of axially extending grooves.

2. The humidifying device according to claim 1, wherein the valve comprises elastomer material.

3. The humidifying device according to claim 2, wherein the elastomer material comprises silicone rubber.

4. The humidifying device according to claim 1, wherein the inlet for the supply of the water into the container and the upper part of the container are formed in one piece.

5. The humidifying device according to claim 4, wherein at least the upper part of the container and/or at least the inlet for the supply of the water is made of plastic material.

6. The humidifying device according to claim 1, wherein the container bottom is formed of plastic material.

7. The humidifying device according to claim 6, wherein the plastic material comprises a film.

8. The humidifying device according to claim 6, wherein the plastic material is polyester.

9. The humidifying device according to claim 6, wherein the thickness of the container bottom is in the range from 0.05 to 0.5 mm.

10. A device for humidifying breathing air for artificial respiration of mammals, comprising:
    at least one essentially closed container for receiving water, the container having an interior;
    a first opening for letting non-humidified air into the interior and a second opening for letting out humidified air from the interior, and a water inlet for supplying the water to the container,
    wherein the water inlet is provided in an upper part of the container, which is adjoined by a tube essentially crossing through the container interior, and
    a valve disposed on a free end of the tube that is configured to limit the level of the water supplied via the tube in such a way that the container bottom in the container interior is maintained essentially covered with water,
    including means which, as a function of the level of the water in the container interior, short-circuits the water vapor out of contact with air to be humidified above the surface of the water in the manner of a bypass between the inlet of non-humidified air and the outlet of the humidified air, and reestablishes contact when the level of water drops in the container interior.

11. The humidifying device according to claim 10, wherein the means includes a float device, which floats in the water in the container interior and when the predetermined level of water is reached, bumps against a first sealing element connected to the container, and thereby interrupts the supply of water into the container.

12. The humidifying device according to claim 11, wherein the float device has a radially oriented sealing face on a top portion thereof forming a collarlike element configured to bump against the first sealing element connected to the container.

13. The humidifying device according to claim 12, wherein, when the collarlike element bumps against the first sealing element, the inlet of the air into the container and the outlet of the air out of the container is essentially short-circuited via a remaining space in the container interior.

14. The humidifying device according to claim 11, wherein the tube extends essentially into the bottom region of the container.

15. The humidifying device according to claim 14, wherein the tube is a central tube in the container, and wherein the float device has an essentially central passage into which the central tube extends.

16. The humidifying device according to claim 11, wherein the float device comprises an essentially closed, floatable body.

17. The humidifying device according to claim 12, wherein the collarlike element comprises a part that is separate from the float element and is secured to the float element.

18. The humidifying device according to claim 11, further comprising a second sealing element disposed essentially centrally to the upper part of the container and essentially circular in cross section.

19. The humidifying device according to claim 18, wherein the second sealing element includes an essentially encompassing sealing lip.

20. The humidifying device according to claim 19, wherein the sealing lip, when the container interior functions in the manner of the bypass, rests sealingly on the float device.

21. The humidifying device according to claim 19, wherein at least the sealing lip comprises an elastomer material.

22. The humidifying device according to claim 12, wherein the collarlike element of the float device comprises an elastomer material.

23. The humidifying device according to claim 11, wherein the float device essentially comprises plastic material.

* * * * *